(12) United States Patent
Koyano et al.

(10) Patent No.: US 7,086,283 B2
(45) Date of Patent: Aug. 8, 2006

(54) EXPLOSION-PROOF PORTABLE GAS DETECTOR

(75) Inventors: Junichi Koyano, Tokyo (JP); Shuji Tajima, Tokyo (JP)

(73) Assignee: Riken Keiki Co., Ltd., Tokyo (JP)

( * ) Notice: Subject to any disclaimer, the term of this patent is extended or adjusted under 35 U.S.C. 154(b) by 83 days.

(21) Appl. No.: 10/892,985

(22) Filed: Jul. 15, 2004

(65) Prior Publication Data

US 2006/0010974 A1    Jan. 19, 2006

(51) Int. Cl.
  *G01P 1/02* (2006.01)
  *G01L 19/14* (2006.01)

(52) U.S. Cl. .................. 73/431; 73/23.31; 73/31.05; 73/31.02; 73/31.03

(58) Field of Classification Search ........... 73/23.2, 73/23.31, 31.05, 31.02, 431, 31.03
See application file for complete search history.

(56) References Cited

U.S. PATENT DOCUMENTS 6,606,897 B1 * 8/2003 Koyano et al. .............. 73/23.2
6,754,067 B1 * 6/2004 Turner et al. ................ 361/659
2003/0138329 A1 * 7/2003 Koyano et al. ................ 417/63

FOREIGN PATENT DOCUMENTS

| JP | 08-007901 A | 1/1996 |
| JP | 2000-209250 A | 7/2000 |
| JP | 2001-176366 A * | 6/2001 |
| JP | 2002-309097 A | 10/2002 |
| JP | 2003-314184 | 9/2003 |

* cited by examiner

*Primary Examiner*—Daniel S. Larkin
(74) *Attorney, Agent, or Firm*—Frishauf, Holtz, Goodman & Chick, P.C.

(57) ABSTRACT

The invention provides an explosion-proof portable gas detector that is easy to be fabricated as a small-sized one handy to carry and high in convenience for use, and has explosion-proofness sufficient in a countermeasure against static electricity and high in reliability. The explosion-proof portable gas detector has at least gas sensors, a signal processing circuit, a display mechanism and a power source part within a housing in the form of a slim and flat box holdable by grasping with a hand. The whole or a part of the housing is formed of a static charge-controlling resin material having an insulating resistance value of at most 1 GΩ and a comparative tracking index of at least 90 V.

19 Claims, 8 Drawing Sheets

EXPLOSION-PROOF PORTABLE GAS DETECTOR

BACKGROUND OF THE INVENTION

1. Field of the Invention

The present invention relates to an explosion-proof portable gas detector, and particularly to an explosion-proof portable gas detector equipped with a gas sucking means for introducing a gas to be detected into it and capable of detecting plural kinds of gas components.

2. Description of the Background Art

There are generally frequent occasions when it may be possible in, for example, underground job sites or gateways, or other places where persons enter, or working regions that air in an environmental atmosphere is in a dangerous state, or will become a dangerous state, such as occasions when hazardous gases such as carbon monoxide and hydrogen sulfide gases may possibly be contained in air in such an environment, or when the oxygen gas concentration in air may possibly be lowered.

When the air in the environmental atmosphere has become a dangerous state to persons due to high concentration of the dangerous gases contained or low oxygen gas concentration, it is necessary to immediately sense the fact.

From such a demand, there have heretofore been proposed various types of portable gas detectors.

Such a portable gas detector is generally used by being fitted to a person's body by means of, for example, a proper fitting member to carry it together with the person's body by this person. However, static electricity is charged on a housing made of, for example, a resin making up the portable gas detector due to, for example, friction of its surface in a working site, and so there is a possibility that firing may be caused by this static electricity.

The portable gas detector is thus required to have a structure capable of avoiding such a possible hazard, specifically, a structure satisfying, for example, the following conditions (a) to (c):

Condition (a): the degree of an insulation resistance value of a resin making up a portable gas detector is not higher than a certain value;

Condition (b): the extent of a surface area of a continuous portion composed of a resin is not greater than a certain value; and Condition (c): the degree of a comparative tracking index as an index, for example, to dielectric breakdown resistance in relation with equipment voltage is not lower than a certain value.

The term "comparative tracking index" as used herein means a value measured in accordance with IEC standard 60112 (Method for the determination of the comparative tracking indices and the tracking indices of solid insulating materials under wet conditions).

Various static charge-controlling resin materials have heretofore been proposed as resin materials forming housing (see, for example, Japanese Patent Application Laid-Open No. 2002-309097). However, those satisfying all the above-described conditions (a) to (c) are not known, and a structure, to which a measure against static electricity is taken so as to satisfy the standard of explosion-proofness as to a portable gas detector used under an environment having a danger of catching fire, is formed by, for example, using a resin material satisfying the condition (a) and controlling the extent itself of a surface area of a continuous resin portion of the housing small so as to satisfy the conditions (b) and (c) (see, for example, Japanese Patent Application Laid-Open No. 2000-209250).

In addition, a measure to ensure explosion-proofness is also taken to members surrounding spaces, in which a power source part for supplying power to functional members related to gas detection, and other members having explosive energy are arranged.

For example, a portable gas detector driven by a battery, in which a battery pack obtained by coating all of a plurality of rod-like batteries (storage batteries) and an insulating spacer with a silicone rubber envelope in a state the batteries have been arranged in parallel in such a manner that different poles adjoin each other to be connected in series, and the insulating spacer has been intervened between the batteries is used, whereby a power source part is provided as an explosion-proof structure, is known (see, for example, Japanese Patent Application Laid-Open No. 7901/1996).

SUMMARY OF THE INVENTION

The present invention has been made on the basis of the foregoing circumstances and fundamentally has as its object the provision of an explosion-proof portable gas detector that is easy to be fabricated as a small-sized one handy to carry and high in convenience for use, and has explosion-proofness with high reliability owing to sufficient countermeasure against static electricity.

According to the present invention, there is thus provided an explosion-proof portable gas detector comprising: at least one gas sensor, a signal processing circuit for processing output signals from the gas sensors, a display mechanism for displaying the result of gas detection by the gas sensors and a power source part for driving the signal processing circuit and display mechanism, arranged within a housing in the form of a slim and flat box holdable by grasping with a hand.

Wherein the whole or a part of the housing is formed of a static charge-controlling resin material having an insulating resistance value of at most 1 G$\Omega$ and a comparative tracking index of at least 90 V.

In the explosion-proof portable gas detector according to the present invention, it may be preferable that the static charge-controlling resin material contains a mixed resin component composed of a combination of a component (A) composed of a thermoplastic resin, a component (B) composed of a thermoplastic resin incompatible with the component (A) at a molecular level and a component (C) composed of any other thermoplastic resin than the components (A) and (B), which has a polar group, and a component (D) composed of a metal salt formed by a cation derived from an alkali metal or alkaline earth metal and an anion capable of ionically dissociating, wherein a proportion of the component (C) is 45 down to 2% by weight based on the mixed resin component, and a proportion of the component (D) per 100 parts by weight of the mixed resin component is 0.01 to 5 parts by weight.

In the explosion-proof portable gas detector according to the present invention, the static charge-controlling resin may preferably be such that the resin components of both component (A) and component (B) are in a state dispersed in a structural unit diameter ranging from 50 nm to 500 $\mu$m when the thermoplastic resin making up the component (A) and the thermoplastic resin making up the component (B) are melted and kneaded at a temperature higher than the melting temperatures of the respective components.

In the explosion-proof portable gas detector according to the present invention, the housing may be formed of a molded product of the static charge-controlling resin material.

The explosion-proof portable gas detector according to the present invention may be so constructed that a gas suction pump to feed a gas to be detected from the outside to the gas sensors by suction is provided within the housing.

In the explosion-proof portable gas detector according to the present invention, the detector may also be so constructed that a plurality of gas sensors including at least a gas sensor composed of a contact combustion type gas sensor element are provided, and electrical power of 4.5 V is supplied from the power source part.

In the explosion-proof portable gas detector according to the present invention, the detector may further preferably be so constructed that a foreside half portion in the interior of the housing is provided as a functional part region, in which functional members related to a gas detecting operation are arranged, and a rear half portion in the interior of the housing is provided as a battery part region, in which a power source for driving the functional members is arranged, wherein a battery chamber is formed in the battery part region in the interior of the housing so as to be opened to the back surface of the housing, and either one of 3 rod-like dry cells or a chargeable battery pack formed by holding 3 chargeable batteries having the same external shape as the dry cell by a holding frame member in a state arranged in parallel is installed in the battery chamber exchangeably with the other.

Still further, in the explosion-proof portable gas detector according to the present invention, the detector may preferably be so constructed that terminals for charging for the chargeable battery pack are provided on the housing in a state exposed to the external surface thereof.

Yet still further, in the explosion-proof portable gas detector according to the present invention, it may be preferable that the chargeable battery pack used be such that a positive terminal is formed at one end thereof, and a negative terminal is formed at the other end, and the detector has a function of judging which of the dry cells or the chargeable battery pack is installed in a battery chamber by detecting the number of terminals that electrical connection has been achieved.

According to the explosion-proof portable gas detector of the present invention, the housing fundamentally has the form holdable by grasping with a hand, and all the necessary component members are rationally arranged in a state that a dead space within the housing is reduced as much as possible, so that the gas detector itself can be fabricated into a small-sized one while surely retaining necessary functions. Accordingly, excellent portability and high convenience for use are achieved.

In addition, since a part or the whole of the housing is formed by the specific static charge-controlling resin material having an insulating resistance value of at most 1 GΩ and a comparative tracking index of at least 90 V, the portable gas detector can be provided as one having excellent explosion-proofness by the static charge-controlling property of the specific static charge-controlling resin material itself.

Further, since the resins as the base materials of the specific static charge-controlling resin material are thermoplastic resins, the resin material has excellent moldability, whereby the housing or parts thereof can be used as molded products. In addition, since the resin material has excellent dielectric breakdown resistance, and its insulation resistance value is sufficiently small compared with resin materials used heretofore as suitable materials, an excellent static charge-controlling effect is developed. Accordingly, the explosion-proof portable gas detector can be constructed as one having excellent explosion-proofness even when the surface area of continuous resin portions in the housing or component parts thereof is great.

Further, since the housing or parts thereof can be integrally molded, the number of parts making up the gas detector can be reduced, so that a portable gas detector having excellent explosion-proofness can be provided at low cost.

Still further, the member surrounding the space, in which the power source part and signal processing circuit are arranged, is formed by the specific static charge-controlling resin material, whereby the gas detector can be fabricated as one having an explosion-proof structure still higher in reliability.

BRIEF DESCRIPTION OF THE DRAWINGS

The above and other objects, features and advantages of the present invention will become apparent from the following description and the appended claims, taken in conjunction with the accompanying drawings, in which:

DETAILED DESCRIPTION OF THE PREFERRED EMBODIMENTS

The present invention will hereinafter be described with reference to the drawings.

Figure 1:
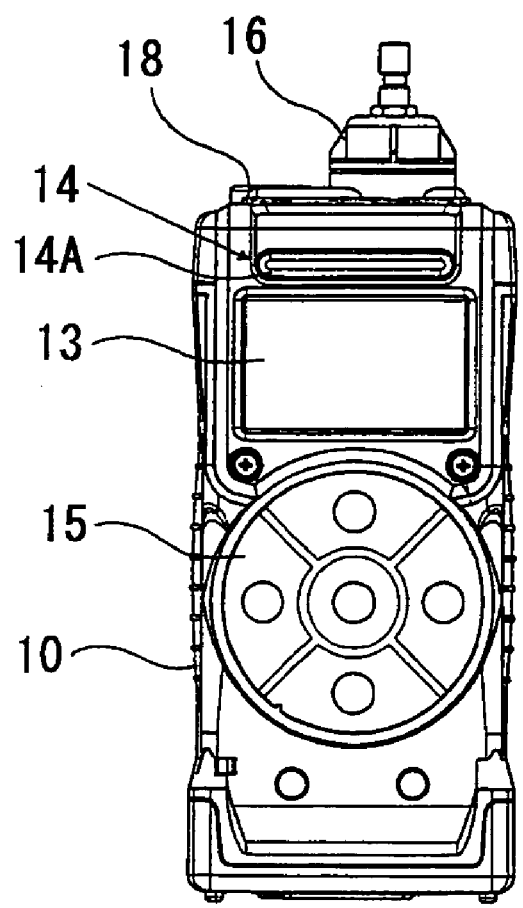
FIG. 1 is a front elevation illustrating the appearance of a constructional example of an explosion-proof portable gas detector according to the present invention.
Figure 2:
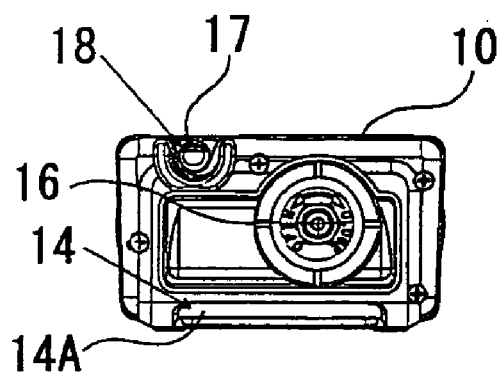
FIG. 2 is a top view of the explosion-proof portable gas detector shown in FIG. 1.
Figure 3:
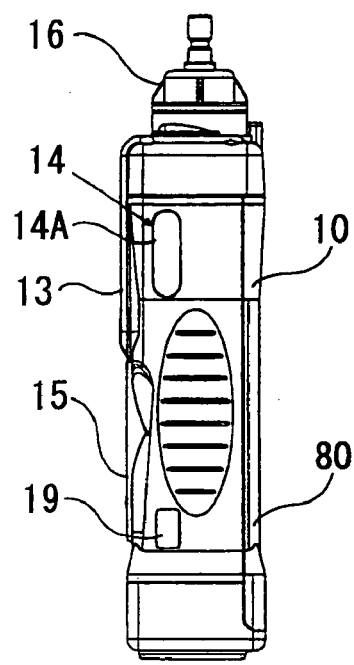
FIG. 3 is a right side elevation of the explosion-proof portable gas detector shown in FIG. 1.
Figure 4:
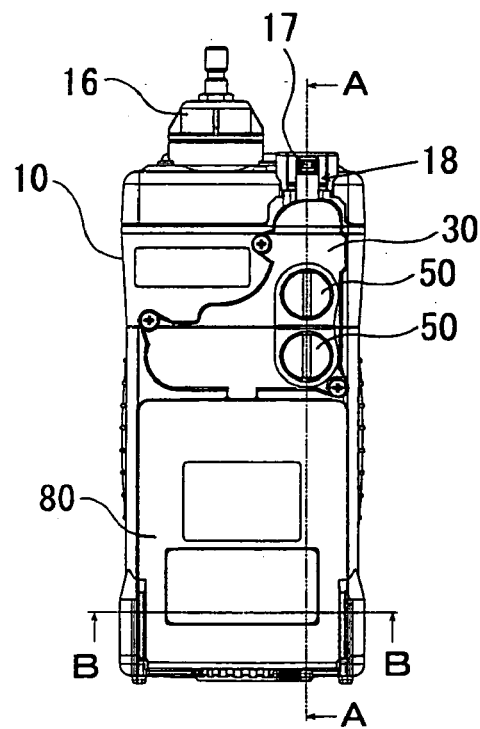
FIG. 4 is a back elevation of the explosion-proof portable gas detector shown in FIG. 1.
Figure 5:
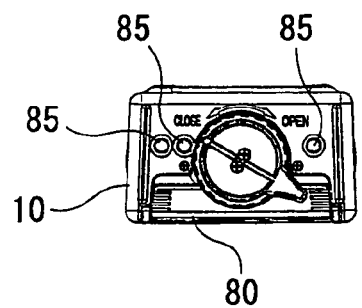
FIG. 5 is a bottom view of the explosion-proof portable gas detector shown in FIG. 1.
Figure 6:
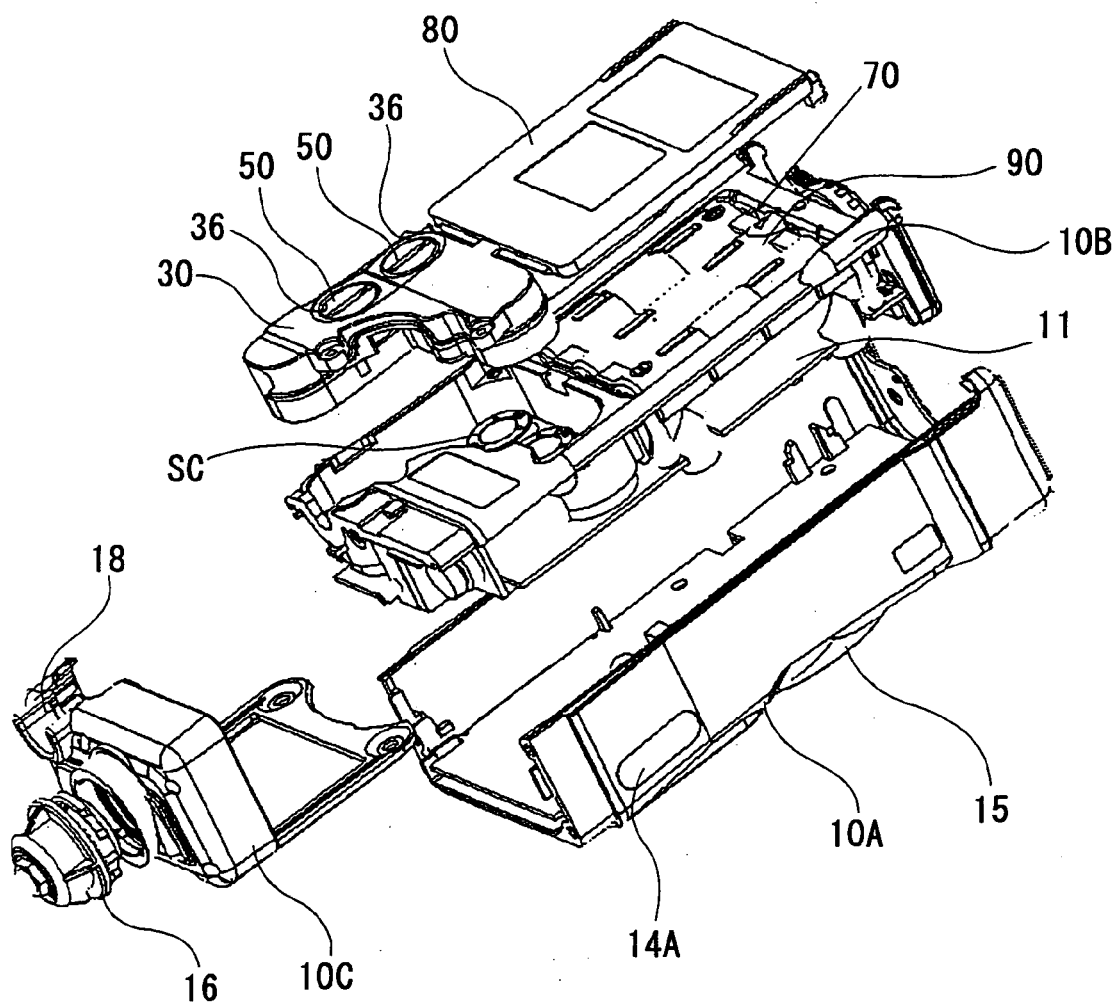
FIG. 6 is an exploded perspective view of the explosion-proof portable gas detector shown in FIG. 1.
Figure 7:
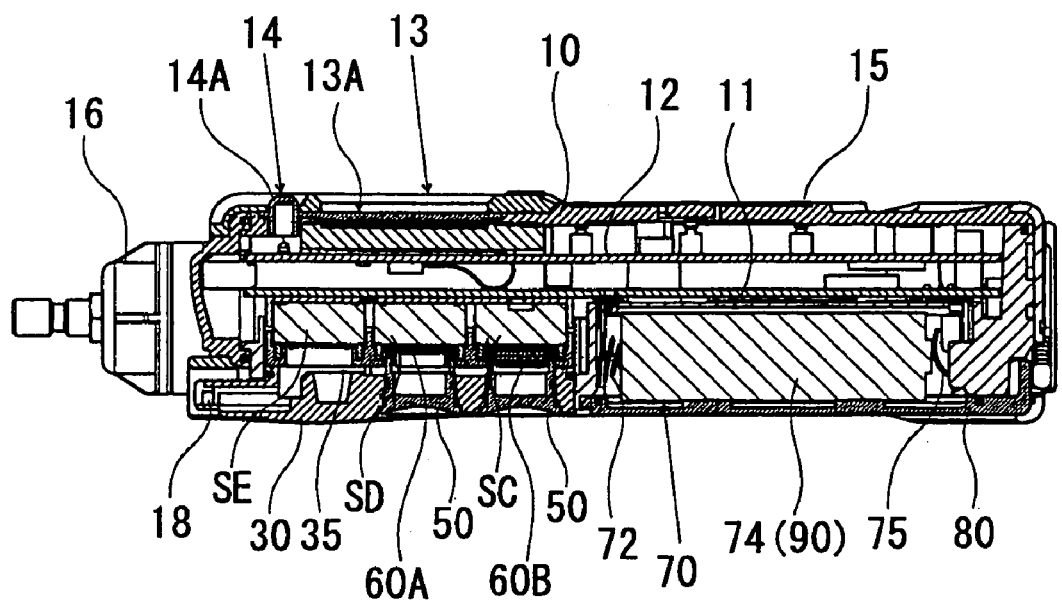
FIG. 7 is a cross-sectional view taken along line A—A in FIG. 4.
Figure 8:
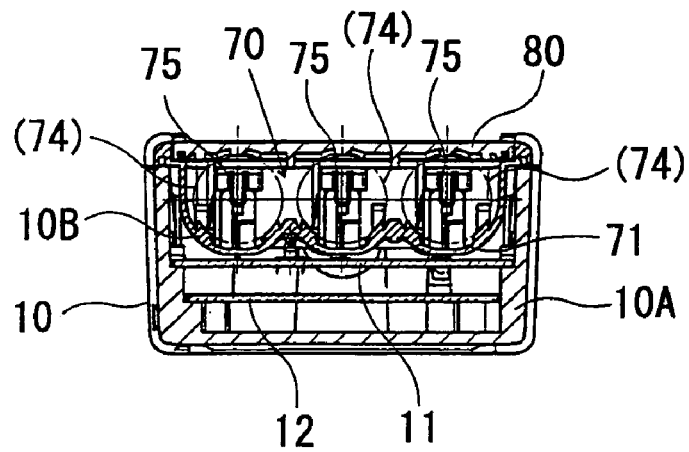
FIG. 8 is a cross-sectional view taken along line B—B in FIG. 4.

FIG. 1 is a front elevation illustrating the appearance of a constructional example of an explosion-proof portable gas detector according to the present invention, FIG. 2 is a top view of the explosion-proof portable gas detector shown in FIG. 1, FIG. 3 is a right side elevation of the explosion-proof portable gas detector shown in FIG. 1, FIG. 4 is a back elevation of the explosion-proof portable gas detector shown in FIG. 1, FIG. 5 is a bottom view of the explosion-proof portable gas detector shown in FIG. 1, FIG. 6 is an exploded perspective view of the explosion-proof portable gas detector shown in FIG. 1, FIG. 7 is a cross-sectional view taken along line A—A in FIG. 4, and FIG. 8 is a cross-sectional view taken along line B—B in FIG. 4.

This explosion-proof portable gas detector (hereinafter referred to as "gas detector" merely) is equipped with a housing 10 in the form of a slim and flat box holdable by grasping with a user's hand. The housing 10 is formed by a rectangular frame-like housing body 10A as shown in FIGS. 6 and 8, a battery case 10B as shown in FIGS. 6 and 8, fitted into an opening on the back surface side of the housing body 10A as shown in FIGS. 6 and 8, a foreside case 10C fitted into the foreend or distal end portion of the housing body 10A, and a cover lid 80 for a battery chamber 70 closely fitted into an opening opened to the back surface of the battery chamber 70 formed at a rear half portion of the battery case 10B.

On the front side in the interior of the housing 10, a circuit board 11 as shown in FIGS. 6 and 8. for control including a gas detection signal-processing circuit for processing signals from gas sensors and a circuit board 12 as shown in FIGS. 7 and 8, including a circuit for power supply and a circuit for charging are arranged in parallel with each other so as to extend along the flat surface of the housing 10. A foreside or distal side half portion in the interior of the housing 10 is provided as a functional part region, in which functional members related to a gas detecting operation are arranged, and a rear or proximal half portion in the interior of the housing 10 is provided as a battery part region, in which a power source part is arranged.

In FIGS. 1 to 4, reference numeral 16 indicates a filter unit for introducing air in an object space in a state that dust has been removed, and reference numeral 18 designates a gas discharging part equipped with a gas discharging port 17 opened to the back surface.

On the front side of the circuit board 11 for control in the functional part region, a panel-like display mechanism 13A composed of, for example, a liquid crystal display panel, on which the kinds and concentrations of gases detected are displayed, is arranged, whereby a display part 13 is formed in the front surface of the housing 10, and light emitting parts 14 for alarm are formed respectively in a foreend or distal end surface and a front region continued therefrom, and both side surface regions of the housing 10. The light emitting parts 14 for alarm are each formed by a light source composed of a light emitting diode (not illustrated) and an aperture plate 14A held by the housing 10 so as to cover the light source.

An operating button 15 is provided at a rear half portion in the front surface of the housing 10.

On the back side of the circuit board 11 for control in the functional part region, are arranged a plurality of gas sensors and a pump unit that is a gas sucking means to successively feed a gas to be detected from the outside to the respective gas sensors by suction.

Figure 9:
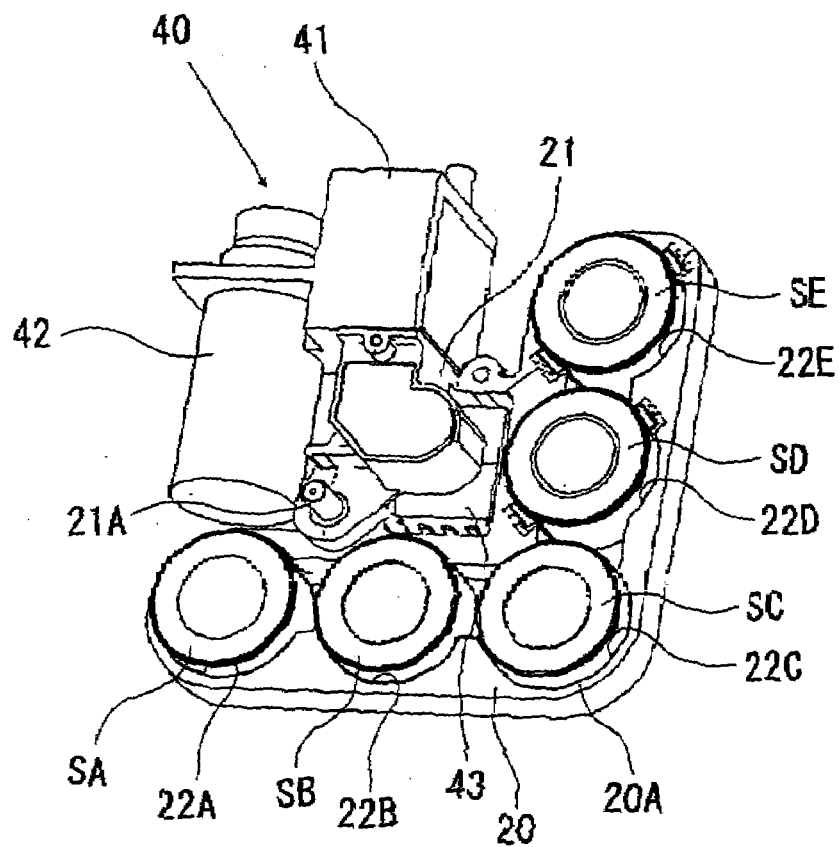
FIG. 9 is a perspective view illustrating the construction of a sensor holder in a state that gas sensors and a pump unit have been installed in the sensor holder.

Specifically described, as illustrated in FIG. 9, 5 button type gas sensors SA to SE are received to a sensor holder 20 having a gas sensor-arranging region of an L shape as a whole, and the pump unit 40, which is a gas sucking means, is installed and arranged in a pump unit-installing part 21 formed at a corner approaching the gas sensor-arranging region in a region the 2 directions of which is sectioned by the gas sensor-arranging region.

The sensor holder 20 is formed of a substantially L-shaped plate as a whole, a gas sensor-receiving recess 22C is formed at a curved portion 20A thereof, and 2 gas sensor-receiving recesses 22A and 22B and 2 gas sensor-receiving recesses 22D and 22E are formed in a row in lateral and vertical directions of the gas sensor-receiving recess 22C, respectively, whereby the L-shaped gas sensor-arranging region is formed. This sensor holder 20 is fixed and arranged on the circuit board 11 for control.

A sensor cap 30 is installed from the back side in recess formed in the foreside half portion of the battery case 10B so as to expose the gas sensors SA to SE, thereby the respective gas sensors SA to SE are held in a state fixed.

In the interior of the sensor cap 30, a gas flowing path 35 for successively feeding a gas to be detected to the each of gas sensors SA to SE is formed, and filter-installing parts 36 are formed at respective positions corresponding to the gas sensor SC for detecting carbon monoxide gas arranged at the curved portion 20A of the gas sensor-arranging region and the gas sensor SD for detecting hydrocarbon gases in a measurement range of % LEL, which is arranged adjacently to the gas sensor SC on the downstream side of the flowing direction of a gas to be detected.

In the filter-installing parts 36 in the sensor cap 30, a filter unit 50 for removal of interfering gases having a function of adsorbing any other interfering gas components than the object gas component to be detected by the gas sensors is installed.

Figure 10:
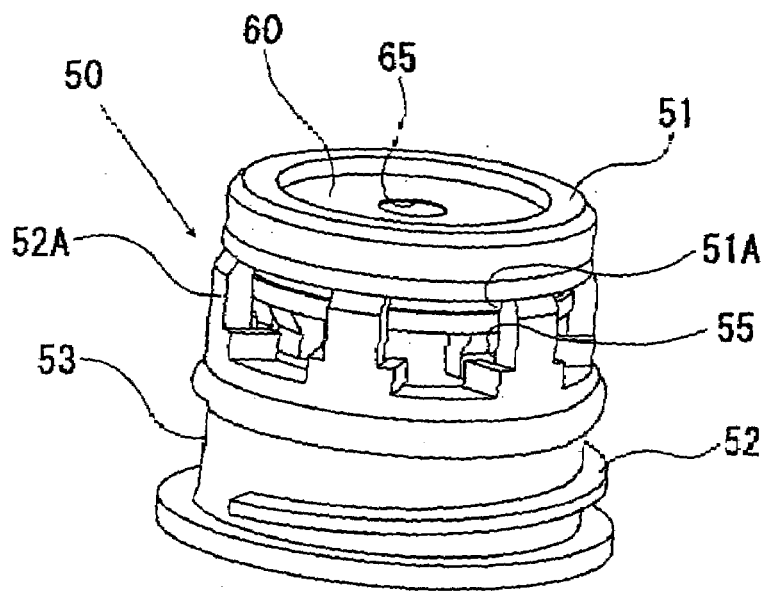
FIG. 10 is a perspective view illustrating the construction of a filter unit for removal of interfering gas components.

As illustrated in FIG. 10, the filter unit 50 for removal of interfering gases is formed by a filter laminate 60, which adsorbs and removes an interfering gas component related to the gas sensors, a filter holder 51 holding the filter laminate 60, and a filter cap 53 composed of, for example, a transparent resin and having the form of a substantially cylinder with bottom, on the peripheral wall of which a projected portion 52 fitting to a spiral groove formed in an inner peripheral wall of the filter-installing part 36 is formed. Engaging claws 52A formed at an opening edge of the filter cap 53 so as to project and extend outward are engaged with a circular groove 51A formed at an end-side portion in the peripheral wall of the filter holder 51, whereby the filter holder 51 is detachably fitted to the filter cap 53.

In the state that the filter holder 51 has been fitted to the filter cap 53, the projected portion 52 of the filter cap 53 is screwed into the spiral groove of the filter-installing part 36 in the sensor cap 30, whereby the whole filter unit 50 for removal of interfering gases is detachably fitted into the sensor cap 30. Reference numeral 55 indicates openings for introducing a gas, and these openings are formed at plural positions in a state separated from each other in a peripheral direction.

The filter laminate 60 is formed by, for example, stacking functional membranes having at least a function of adsorbing the interfering gas component related to the gas sensors in a state intervened between 2 outer membranes.

Figure 11:
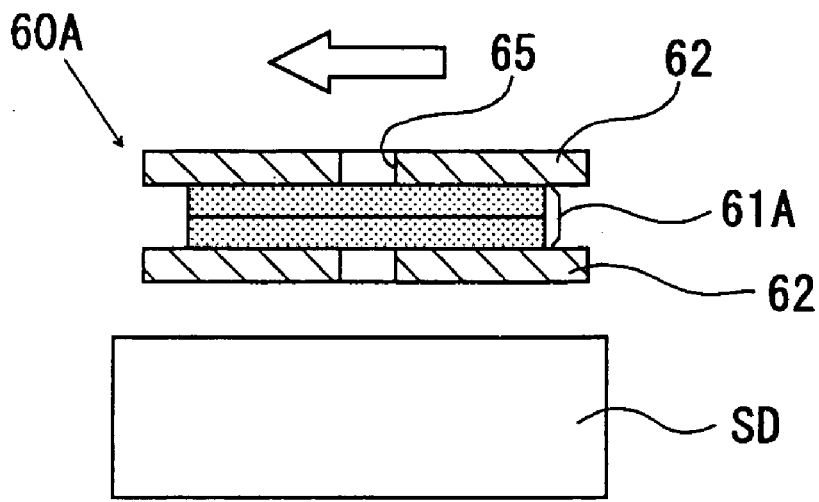
FIG. 11 is a cross-sectional view illustrating the construction of an exemplary filter laminate related to a gas sensor for detecting hydrocarbon gases in a measurement range of % LEL.

For example, that formed by stacking functional membranes 61A for adsorbing the interfering gas in a state intervened between 2 outer membranes 62, 62 composed of, for example, Teflon (registered trademark) as illustrated in FIG. 11 is used as the filter laminate 60A related to the gas sensor SD for detecting hydrocarbon gases in the measurement range of % LEL. In this embodiment, the functional membrane 61A has the 2-layer structure. However, no particular limitation is imposed on the number of membranes laminated.

Figure 12:
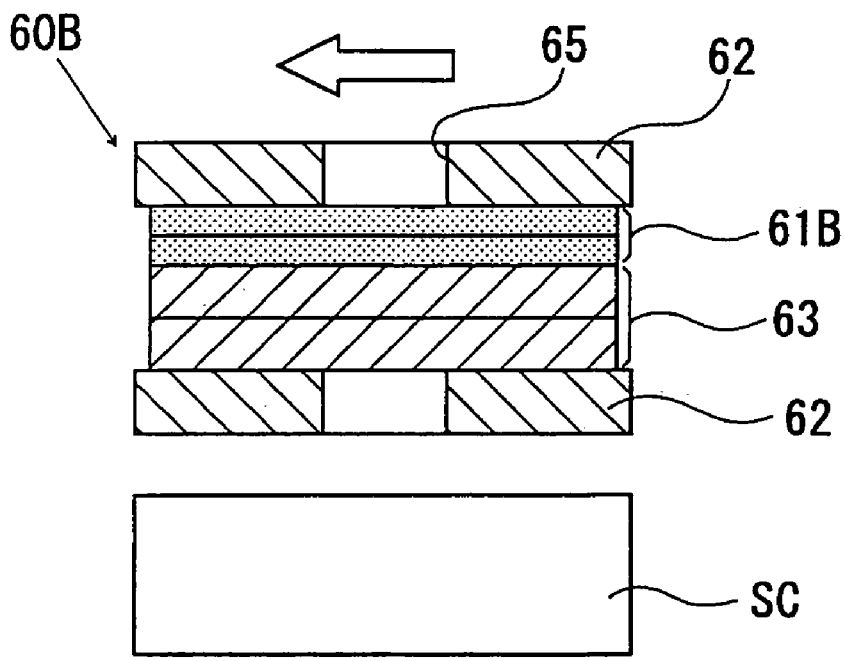
FIG. 12 is a cross-sectional view illustrating the construction of an exemplary filter laminate related to a gas sensor for detection of carbon monoxide gas.

The filter laminate 60B related to the gas sensor SC for detecting carbon monoxide gas is formed by stacking functional membranes 61B for adsorbing, for example, hydrogen sulfide gas, which is an interfering gas component, and active carbon layers 63 located on a lower side of the functional membranes 61B in a direction introducing a gas to be detected in a state intervened between 2 outer membranes 62, 62 as illustrated in FIG. 12. In this embodiment, 2 layers of the each functional membrane 61B and active carbon layer 63 are stacked. However, no particular limitation is imposed on the number of membranes and layers laminated. An arrow in FIGS. 11 and 12 indicates a flowing direction of a gas to be detected.

A viewing hole 65 for checking the degree of stain of the functional membrane 61A or 61B visually is formed in a part, for example, a central portion, of each of the outer membranes 62, 62 making up the filter laminate 60A or 60B, whereby the degree of stain of the functional membrane 61A or 61B can be checked visually from the outside even in a state that the filter unit 50 for removal of interfering gases is fitted to the sensor cap 30, since the filter cap 53 has transparency, so that the time the filter laminate 60 is exchanged can be easily known.

In the gas detector described above, at least one of the 5 gas sensors SA to SE is composed of a contact combustion type gas sensor element for detection of, for example, inflammable hydrocarbon gases, and power of 4.5 V is supplied from the dry cells 74 or the chargeable battery pack 90 making up the power source part.

As an example of a combination of the gas sensors, a gas sensor SA for detecting oxygen gas, which is composed of, for example, a galvanic cell type gas sensor element, a gas sensor SB for detecting hydrogen sulfide gas, which is composed of, for example, a controlled potential electrolysis type gas sensor element, a gas sensor SC for detecting carbon monoxide gas, which is composed of, for example, a controlled potential electrolysis type gas sensor element, a gas sensor SD for detecting hydrocarbon gases in a measurement range of % LEL concentration (level of explosion limit), which is composed of, for example, a contact combustion type gas sensor element, and a gas sensor SE for detecting hydrocarbon gases in a measurement range of volume %, which is composed of, for example, a thermal conductivity type gas sensor element, are used in order from the upstream side of a flowing direction of a gas to be detected.

The pump unit-installing part 21 functions as a gas flowing path-forming member, and a gas to be detected ejected from a gas suction pump 41 is ejected from a gas-ejecting pipe 21A provided so as to project and extend upward through a gas flowing path formed within the pump unit-installing part 21. In the present invention, for example, a pipe, the opening diameter of which is smaller than the inner diameter of the gas flowing path, is used as the gas-ejecting pipe 21A, whereby the gas to be detected is ejected in a pressurized state.

The pump unit 40 is formed by a gas suction pump 41 installed at a foreend of the pump unit-installing part 21 in the sensor holder 20, a pump-driving motor 42 arranged along a side surface of the pump unit-installing part 21 in such a manner that a driving shaft thereof extends in foreside and rear directions, and a pressure sensor 43 for detecting the exhaust pressure of a gas to be detected, and is rationally arranged in a state that portions projected from a peripheral edge of the circuit board 11 for control, specifically, the front and side edges of the circuit board 11 for control are substantially not present.

In the present invention, that having performance capable of feeding a gas to be detected at a flow rate of, for example, 0.2 to 0.5 liters/min is used as the gas suction pump 41.

In this gas detector, when the flow rate of a gas introduced is lowered due to, for example, suction of water, and lowering of the exhaust pressure of the gas to be detected is detected by the pressure sensor 43, the driving of the gas suction pump 41 is forcedly stopped.

As described above, the rear half portion in the interior of the housing 10 is provided as the battery part region, in which the power source part is arranged. In this battery part region, the battery chamber 70, in which either of 3 AA-sized (ANSI standard) dry cells 74 or a chargeable battery pack 90, which will be described subsequently, is installed exchangeably with the other, is formed.

As illustrated in FIGS. 7 and 8, a receiving and supporting part 71, which comes into contact with a part of a peripheral surface of each of the dry cells 74, 74, 74 to support it, is formed in the battery chamber 70. On a foreend surface of the battery chamber 70, are arranged 3 negative-side terminal armatures 72, 72, 72 corresponding to the respective dry cells 74, 74, 74, and 3 positive-side terminal armatures 75, 75, 75 are arranged on a rear end surface thereof oppositely to the negative-side terminal armatures 72, 72, 72.

The respective dry cells 74, 74, 74 are installed in the receiving and supporting part 71 in a state that the positive electrodes and negative electrodes thereof are turned to the same directions as one another, so as to be connected in series by connecting armatures (not illustrated) arranged so as to extend along the longitudinal direction of the dry cell.

Figure 13:
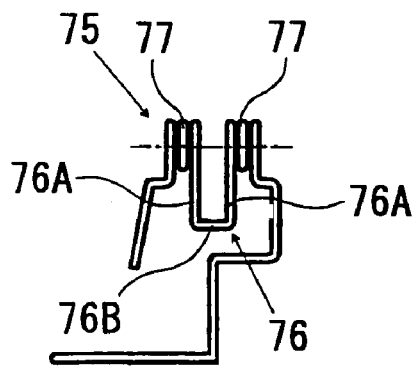
FIG. 13 is a front elevation illustrating the construction of a positive-side terminal armature.
Figure 14:
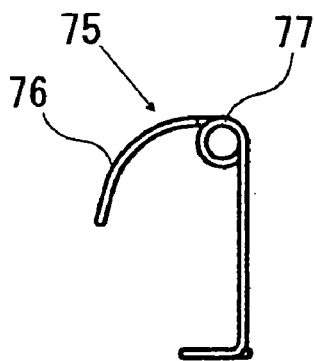
FIG. 14 a side elevation of the positive-side terminal armature shown in FIG. 13.
Figure 15:
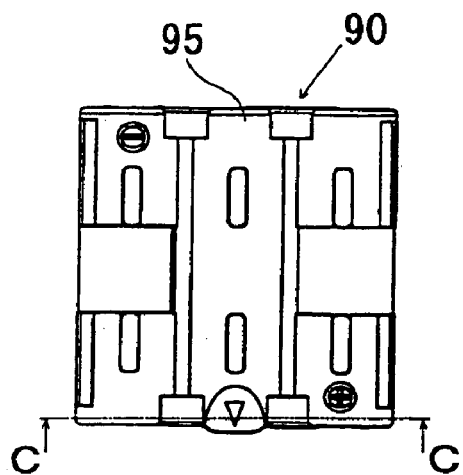
FIG. 15 is a plan view illustrating the construction of an exemplary chargeable battery pack.
Figure 16:
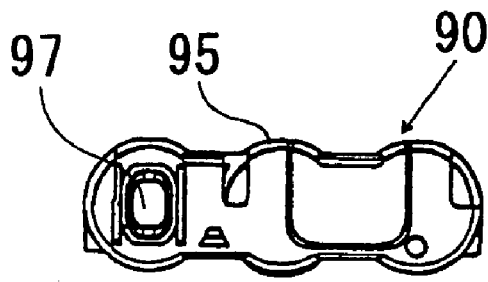
FIG. 16 is a foreside view of the chargeable battery pack shown in FIG. 15.
Figure 17:
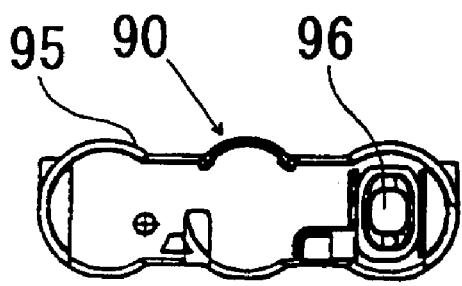
FIG. 17 is a rear view of the chargeable battery pack shown in FIG. 15.
Figure 18:
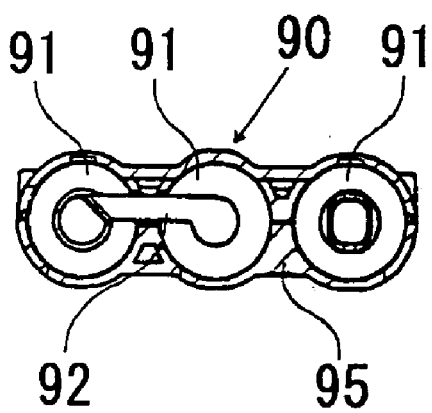
FIG. 18 is a cross-sectional view taken along line C—C in FIG. 15.

As illustrated in FIGS. 13 and 14, the positive-side terminal armature 75 is formed by deforming a metallic wire rod having elasticity and has a reversed U-shaped central contact arm portion 76, which forms a contact with the dry cell 74 or the chargeable battery pack 90, and 2 coil portions 77, 77 respectively connected to both ends of the central contact arm portion 76.

The coil portions 77, 77 each have the same center axis extending in a direction normal to the longitudinal direction of the dry cell.

The central contact arm portion 76 is of a reversed U shape composed of 2 parallel portions 76A, 76A and a linking arc portion 76B for linking both tips of the parallel portions 76A, 76A to each other. The 2 parallel portions 76A, 76A are greatly projected outward in a radial direction of the coil portions 77, 77 and curved in the form of an arc in a plane normal to the center axis of the 2 coil portions 77, 77. Specifically, the 2 parallel portions 76A, 76A are curved on an axis extending in parallel with the center axis of the coil portions 77, 77 and along a peripheral surface of a column having a diameter greater than the coil portions 77, 77.

No particular limitation is imposed on the negative-side terminal armature 72, and it is formed by, for example, a spiral type spring armature heretofore used.

The displacement by the positive-side terminal armature 75 in the longitudinal direction of the dry cell 74 is set in such a manner that the size of excess dimensions of the chargeable battery pack 90 to the dry cells 74 can be absorbed by displacement without greatly increasing the size of the terminal armature itself compared with the spiral type spring armature. When the total degree of displacement by the positive-side terminal armature 75 and the negative-side terminal armature 72 is, for example, at least 5 mm, the chargeable battery pack 90 can be surely installed in a state that sufficient electrical connection has been achieved.

As illustrated in FIGS. 15 to 18, the chargeable battery pack 90 is formed by integrally holding 3 rod-like chargeable batteries (storage batteries) 91, 91, 91 having the same external form as the AA-sized (ANSI standard) dry cell 74 by a holding frame member 95 in a state that the positive electrodes and negative electrodes of batteries adjacent to each other have been turned to reverse directions to each other so as to be connected in series by connecting armatures 92.

The holding frame member 95 has a sectional form adapted to the form of a space in a section crossing at a right angle to the longitudinal direction of the battery chamber. A positive terminal 96 is formed at a rear end surface (lower end surface in FIG. 15) thereof, and a negative terminal 97 is formed at a foreend surface (upper end surface in FIG. 20) thereof.

In the gas detector described above, terminals 85 for charging for the chargeable battery pack are formed on, for example, a rear end surface of the housing 10 in an exposed state as illustrated in FIG. 5, whereby a charging operation can be conducted in a state that the chargeable battery pack 90 has been installed in the battery chamber 70 as it is.

The circuit board 11 for control preferably has a function of judging which of the dry cells 74 and the chargeable battery pack 90 is installed in the battery chamber 70 by detecting the number of terminals that electrical connection has been achieved.

Specifically described, when the dry cells 74 are installed in the battery chamber 70, all the 6 terminal armatures are in a state that electrical connection has been achieved. When the chargeable battery pack 90 is installed in the battery chamber 70 on the other hand, 2 terminal armatures are in a state that electrical connection has been achieved. Which of the dry cells 74 and the chargeable battery pack 90 is installed in the battery chamber 70 can be judged by detecting these states. When the dry cells 74 are installed in the battery chamber 70, the dry cells 74 are thereby prevented from being charged even when the gas detector is fitted to a proper battery charger by mistake in a state that the dry cells 74 have been installed. Accordingly, the gas detector can be provided with high safety.

In the gas detector described above, the whole or a part of the housing 10, specifically, the case body 10A, battery case 10B, foreside case 10C and cover lid 80 for battery chamber are formed of molded products of a static charge-controlling resin composition.

<Static Charge-Controlling Resin Composition>

The static charge-controlling resin composition (hereinafter referred to as "specific static charge-controlling resin composition") according to the present invention preferably contains a mixed resin component composed of a combination of a component (A) composed of a thermoplastic resin, a component (B) composed of a thermoplastic resin incompatible with the component (A) at a molecular level and a component (C) composed of any other thermoplastic resin than the components (A) and (B), which has a polar group, and a component (D) composed of a metal salt formed by a cation derived from an alkali metal or alkaline earth metal and an anion capable of ionically dissociating As examples of the thermoplastic resin making up the component (A) of the specific static charge-controlling resin composition, may be mentioned polymers and copolymers of vinyl monomers, such as polyvinyl chloride, polystyrene, (meth)acrylate polymers such as polymethyl methacrylate (PMMA), (meth)acrylate polymers, (meth)acrylic acid polymers, and acrylonitrile-butadiene-styrene terpolymers (ABS resins); poly($\alpha$-olefins) such as low density polyethylene, medium density polyethylene, high density polyethylene, low-pressure-processed low density polyethylene, polypropylene, polybutene-1 and poly(4-methylpentene-1); homopolymers of $\alpha$-olefins and copolymers of an $\alpha$-olefin and any other monomer, such as propylene-ethylene block copolymers and propylene-ethylene random copolymers; polyamides such as nylon 6, nylon 4,6, nylon 6,6, nylon 6,10, nylon 6,12, nylon 11 and nylon 12; polyesters such as polyethylene terephthalate and polybutylene terephthalate; aromatic polyethers such as polyphenylene oxide; polycarbonate; polyimide; and sulfone polymers such as polysulfone and poly(ether sulfone).

Among these, polymers and copolymers of vinyl monomers, such as polyvinyl chloride, polystyrene, (meth)acrylate polymers such as polymethyl methacrylate (PMMA), and acrylonitrile-butadiene-styrene terpolymers (ABS resins); polypropylene; crystalline propylene copolymers such as crystalline propylene-ethylene copolymers and crystalline propylene-butene-1 copolymers; nylon; polybutylene terephthalate; and the like are preferred in that excellent moldability can be obtained; with polymers and copolymers of vinyl monomers, such as polyvinyl chloride, polystyrene, (meth)acrylate polymers being particularly preferred.

In order to obtain, for example, a general-purpose static charge-controlling resin composition, an acrylonitrile-butadiene-styrene terpolymer (ABS resin) is preferred. In order to obtain a static charge-controlling resin composition used in an application field of which transparency is required, a thermoplastic resin having transparency, for example, polymethyl methacrylate (PMMA), polycarbonate or transparent ABS resin is preferred.

Polycarbonate, polyethylene terephthalate, aromatic polyimides, aromatic polyethers and the like are preferred in that excellent heat resistance is achieved.

As the component (B) making up the specific static charge-controlling resin composition, any resin may be used so far as it is a thermoplastic resin incompatible at a molecular level with the thermoplastic resin making up the component (A) used. For example, the component (B) may be selected for use from among the thermoplastic resins mentioned as examples of those making up the component (A). However, a combination that the resin components of both component (A) and component (B) are in a state dispersed in the form of a structural unit whose average structural unit diameter ranges from 50 nm to 500 μm when the component (A) and the component (B) are melted and kneaded at a temperature higher than the melting temperatures of the respective components is preferred.

For example, when an acrylonitrile-butadiene-styrene terpolymer (ABS resin) is used as the component (A), one or a combination of a polystyrene resin and a polycarbonate resin is preferably used as the component (B).

When a polyvinyl chloride resin (PVC) is used as the component (A), one of a methacrylic acid-butadiene-styrene terpolymer (MBS), polymethyl methacrylate (PMMA), an ABS resin and an acrylic rubber or a combination of at least two thereof is preferably used as the component (B).

When polybutylene terephthalate (PBT) is used as the component (A), one or a combination of polyethylene terephthalate (PET) and a polycarbonate resin (PC) is preferably used as the component (B).

When polymethyl methacrylate (PMMA) is used as the component (A), one or a combination of acrylic rubber and a polycarbonate resin is preferably used as the component (B).

When a nylon resin is used as the component (A), one or a combination of an ABS resin and a polycarbonate resin is preferably used as the component (B).

As the component (C) making up the specific static charge-controlling resin composition, any resin may be used so far as it is any other thermoplastic resin than the components (A) and (B) used and has a polar group in its molecular structure. However, for example, a thermoplastic elastomer is preferred.

As examples of the thermoplastic elastomer, may be mentioned poly(ether ester amide) resins, polyester elastomers, aliphatic polyester, polyurethane elastomers and polyamide elastomers. Among these, poly(ether ester amide) resins are preferred.

The thermoplastic resin of the component (C) preferably has a glass transition temperature of 60° C. or lower, more preferably 50° C. or lower, particularly preferably 40° C. or lower, still more preferably 30° C. or lower. If a thermoplastic resin having a glass transition temperature exceeding 60° C. is used as the component (C), it is difficult to provide a resin material having a sufficient static charge-controlling effect.

(C-1) Poly(Ether Ester Amide) Resin:

The poly(ether ester amide) resin used as the component (C) in the specific static charge-controlling resin composition is one of polymeric nonionic surfactants having a polyether segment. As specific examples thereof, may be mentioned static charge-controlling elastomers having polyether segment such as polyethylene glycol-polyamide copolymers, polyethylene glycol-methacrylate copolymers, polyethylene oxide/polypropylene oxide copolymers, polyethylene glycol-containing polyester amide copolymers and polyethylene glycol-containing polyester elastomers.

(C-2) Polyester Elastomer:

The polyester elastomer used as the component (C) in the specific static charge-controlling resin composition is a multi-block copolymer that a hard segment in its molecule is formed by polyester, and a soft segment is formed by a polyether or polyester having a low glass transition temperature (Tg). As specific examples thereof, may be mentioned elastomers of a polyester/polyether type that a hard segment is formed by an aromatic crystalline polyester such as polybutylene terephthalate, and a soft segment is formed by polyether, and elastomers of a polyester/polyester type that a hard segment is formed by an aromatic crystalline polyester, and a soft segment is formed by an aliphatic polyester.

The polyester/polyether type polyester elastomer is synthesized by, for example, a transesterification reaction and a polycondensation reaction using dimethyl terephthalate, and 1,4-butanediol, poly(tetramethylene ether glycol) and the like as starting materials.

The polyester/polyester type polyester elastomer is synthesized by, for example, a transesterification reaction and a ring-opening reaction using dimethyl terephthalate, and 1,4-butanediol, ε-caprolactone and the like as starting materials.

In the specific static charge-controlling resin composition according to the present invention, any of ordinary polyester elastomers may be used. They may be used either singly or in any combination thereof.

(C-3) Aliphatic Polyester:

As the aliphatic polyester used as the component (C) in the specific static charge-controlling resin composition, may also be used a polyester generally marketed as that having biodegradability. As examples thereof, may be mentioned "Bionole" (trade name; product of Showa Highpolymer Co., Ltd.; polybutylene succinate, polybutylene succinate adipate) and "Celgreen" (trade name, product of Daicel Chemical Industries, Ltd.; polycaprolactone). However, any resin may be selected according to uses and properties. Industrially, those synthesized by a dehydration polycondensation reaction and a dediol reaction using an aliphatic dicarboxylic acid and an excessive amount of a diol as starting materials are mentioned. As such aliphatic polyester, polybutylene succinate, polyethylene succinate, or a copolymer thereof is general, and various high-molecular weight type polymers are industrially produced.

Examples of the aliphatic polyester preferably used as the component (C) in the specific static charge-controlling resin composition include polybutylene succinate (binary condensate of succinic acid and 1,4-butanediol) and polybutylene succinate adipate (ternary condensate of succinic acid, adipic acid and 1,4-butanediol).

In the aliphatic polyester, a reactive group such as an isocyanate group or urethane group may also be introduced into its structure. Further, as the aliphatic polyester, may also be used a copolymer such as a copolyester obtained by copolymerizing a polylactic acid or the like.

(C-4) Polyurethane Elastomer:

The polyurethane elastomer used as the component (C) in the specific static charge-controlling resin composition is a thermoplastic elastomer having a urethane group and a linear multi-block copolymer that a soft segment is formed by polyurethane obtained by a reaction of a long-chain glycol and isocyanate, and a hard segment is formed by polyurethane obtained by a reaction of a short-chain glycol and isocyanate. It may also be that obtained by using a crosslinking agent or chain-lengthening agent as needed.

As general classification by the kind of the long-chain glycol, examples of those of a polyether type include polyethylene oxide, polypropylene oxide and copolymers thereof. Examples of those of a polyester type include polyadipate, polylactone and polycarbonate. Examples of those of an aliphatic type include polybutadiene and polyisoprene.

As the short-chain glycol, an aliphatic glycol such as ethylene glycol, 1,4-butanediol or 1,6-hexanediol, an alicyclic glycol such as cyclohexanedimethanol, or an aromatic glycol such as hydroquinonebis(2-hydroxyethyl)-ether is generally used.

On the other hand, as the isocyanate, 4,4'-diphenylmethane diisocyanate (MDI), 2,4'-toluene diisocyanate and/or 2,6-toluene diisocyanate (TDI) is used.

As the crosslinking agent (chain-lengthening agent), is used an aromatic diamine such as 3,3-dichloro-4,4-diaminodiphenylmethane (MOCA).

The polyurethane elastomers mentioned above may be used either singly or in any combination thereof.

(C-5) Polyamide Elastomer:

The polyamide used as the component (C) in the specific static charge-controlling resin composition is a generic designation of amide resins having an amide bond in its repeating units. As specific examples thereof, may be mentioned nylon 6, nylon 6,6, nylon 12, polyamide polyester copolymers and polyamide polyether copolymers.

The polyamide elastomer used as the component (C) in the specific static charge-controlling resin composition is a generic designation of thermoplastic elastomers having a polyamide binding phase that is a hard segment, and a polyether or polyester structure as a soft segment. An polyamide elastomer using, for example, polyamide (PA) 12 ingredient as a PA binding phase is obtained by a process, in which laurolactam, a dicarboxylic acid and poly(ether diol) are reacted by adding water as a lactam ring-opening catalyst under pressurizing and heating to obtain carboxyltelechelic nylon 12 oligomer, and a thermoplastic elastomer is obtained by a condensation reaction of the oligomer and poly(ether diol). Besides, nylon 6 (PA6) or the like may also be used as the polyamide binding phase.

The polyamide elastomer is provided in the form of, in terms of its basic structure, a polyether block polyamide elastomer or poly(ether ester) block polyamide elastomer by the above-described synthetic process. According to the synthetic process, polyamide elastomers having various properties are obtained according to the kind of the diol used, or the like.

A proportion of the component (B) blended in the specific static charge-controlling resin composition is preferably 3 to 50 parts by weight per 50 to 97 parts by weight of the component (A) (wherein the total of the components (A) and (B) is 100 parts by weight), more preferably 20 to 50 parts by weight per 50 to 80 parts by weight of the component (A). If the proportion of the component (B) is too low or too high, it is difficult to obtain a resin material having a sufficient static charge-controlling effect.

A proportion of the component (C) blended is preferably 45 down to 2% by weight based on the mixed resin component, i.e., 45 down to 2 parts by weight per 55 to 98 parts by weight of the total of the components (A) and (B) (wherein the total of the components (A), (B) and (C) is 100 parts by weight), more preferably 35 down to 3 parts by weight per 65 to 97 parts by weight of the total of the components (A) and (B), still more preferably 30 down to 5 parts by weight per 70 to 95 parts by weight of the total of the components (A) and (B). If the proportion of the component (C) blended exceeds 45 parts by weight, the resulting resin material involves problems that molding and processing ability is markedly deteriorated, and the mechanical properties of the matrix resins, the components (A) and (B) are greatly lowered. If the proportion of the component (C) blended is lower than 2 parts by weight on the other hand, the resulting resin material can develop little static charge-controlling ability.

Examples of the alkali metal or alkaline earth metal, which becomes a cation making up the metal salts of the component (D) in the specific static charge-controlling resin composition, include Li, Na, K, Mg and Ca. $Li^+$, $Na^+$ or $K^+$ having a small ionic radius is preferred as the cation.

Examples of the anion capable of ionically dissociating, which makes up the metal salts of the component (D) in the specific static charge-controlling resin composition, include $Cl^-$, $Br^-$, $F^-$, $I^-$, $NO_3^-$, $SCN^-$, $ClO_4^-$, $CF_3SO_3^-$, $BF_4^-$, $(CF_3SO_2)_2N^-$ and $(CF_3SO_2)_3C^-$. As preferable examples thereof, may be mentioned $ClO_4^-$, $CF_3SO_3^-$, $(CF_3SO_2)_2N^-$ and $(CF_3SO_2)_3C^-$.

Metal salts formed by the above-described cations and anions are great in number. Among these, $LiClO_4$, $NaClO_4$, $Mg(ClO_4)_2$, $KClO_4$, $(CF_3SO_3)Li$, $(CF_3SO_2)_2NLi$, $(CF_3SO_2)_2NNa$, $(CF_3SO_2)_3CLi$ and $(CF_3SO_2)_3CNa$ are preferred, with, $LiClO_4$ and $NaClO_4$ being particularly preferred.

A proportion of the component (D) in the static charge-controlling resin composition is preferably 0.01 to 5 parts by weight per 100 parts by weight of the total of the components (A), (B) and (C)(mixed resin component), more preferably 0.05 to 0.5 parts by weight per 100 parts by weight of the total of the components (A), (B) and (C). If the proportion of the component (D) is lower than 0.01 parts by weight, sufficient static charge-controlling ability cannot be imparted to the resulting resin material. If the proportion of the component (D) exceeds 5 parts by weight on the other hand, the static charge-controlling effect cannot be improved, or rather progress of crystallization, deterioration of the resulting material, etc. are incurred, and the static charge-controlling effect is lowered.

Into the static charge-controlling resin composition according to the present invention, additives such as various kinds of fillers, stabilizers, colorants, reinforcing rubber, other elastomer components, plasticizers, dispersing agents, ultraviolet absorbents, antioxidants, flame retardants, reinforcing materials, lubricants, foaming agents, weathering agents (light stabilizers) and metal powder may be suitably blended according to the objects.

The specific static charge-controlling resin composition according to the present invention can be applied to wide application fields of electric and electromechanical members, printer members, scanner members, members for OA apparatus such as copying machines, etc. in addition to the portable gas detectors.

The specific static charge-controlling resin composition according to the present invention can be adopted to all molding methods and can be subjected to molding or forming processing by various kinds of molding or forming machines, for example, an extruder, injection molding machine, blow molding machine, calendering machine, vacuum forming machine and embossing machine.

In molded or formed products of such a specific static charge-controlling resin composition as described above, their insulating resistance values and comparative tracking indices are controlled to at most 1 GΩ and at least 90 V, respectively, whereby these are provided as those having excellent static charge-controlling ability.

In the gas detector described above, a gas to be detected ejected from the gas suction pump 41 is passed through the gas flowing path 35 formed in the interior of the sensor cap 30 and successively fed to the gas sensors SA to SE to conduct detection of the object gases to be detected and the kinds and concentrations of gases detected is displayed on the display part 13. When the fact that the concentration of any object gas to be detected has exceeded a reference value is detected, an alarm is raised by light emission of the light emitting parts 14 for alarm.

For example, the reference value in the case where an object gas to be detected is oxygen gas ($O_2$ gas) is preset to, for example, 18.0% by volume (vol %). When the concentration becomes lower than this reference value, an alarm actuating signal is outputted. The reference value in the case where an object gas to be detected is a hydrocarbon gas (HC gas) is preset to, for example, 10% LEL (gas concentration to a level of explosion limit). The reference value in the case where an object gas to be detected is carbon monoxide gas (CO gas) is preset to, for example, 25 ppm, and the reference value in the case where an object gas to be detected is hydrogen sulfide gas ($H_2S$ gas) is preset to, for example, 10 ppm. When the concentration exceeds any of these reference values, an alarm actuating signal is outputted.

Alarm annunciating mechanisms may take a structure that an alarm buzzer and a vibration generator (emitting low cycles of about several tens Hz) for alarm are provided. In this case, an alarm is raised by buzzer sound by the alarm buzzer, light emission by the light emitting element for alarm and vibration by the vibration generator for alarm, respectively.

When plural kinds of alarm annunciating mechanisms are provided, it is not necessary to drive all the alarm annunciating mechanisms at the same time, and it is preferable to conduct a cyclic alarm operation that the respective alarm annunciating mechanisms are successively driven only for a predetermined period of time. According to such drive control, the consumption of the dry cells or batteries can be inhibited compared with the case where the alarm annunciating mechanisms are driven at the same time.

According to the gas detector described above, the housing 10 fundamentally has the form holdable by grasping with a user's hand, and all the necessary component members are rationally arranged in a state that a dead space within the housing 10 is reduced as much as possible, so that the gas detector itself can be fabricated into a small-sized one while surely retaining necessary functions. Accordingly, excellent portability and high convenience for use can be achieved.

In addition, the case body 10A, battery case 10B, foreside case 10C and cover lid 80 for battery chamber making up the housing 10 are formed by the specific static charge-controlling resin material having an insulating resistance value of at most 1 GΩ and a comparative tracking index of at least 90 V, so that excellent explosion-proofness satisfying the standard of explosion-proofness can be imparted to the gas detector by the static charge-controlling ability of the specific static charge-controlling resin material itself.

Since the base resins of the specific static charge-controlling resin material are thermoplastic resins, it has excellent moldability, whereby the case body 10A, battery case 10B, foreside case 10C and cover lid 80 for battery chamber making up the housing 10 can be used as molded products. In addition, since the specific static charge-controlling resin material has excellent dielectric breakdown resistance, and its insulation resistance value is sufficiently small compared with resin materials used heretofore as suitable materials, an excellent static charge-controlling effect is developed. Accordingly, the gas detector can be constructed as one having excellent explosion-proofness even when the surface area of continuous resin portions in the housing 10 or component parts thereof is greater than the reference value of the explosion-proofness as to portable gas detectors, specifically, for example, 100 cm$^2$ that is a reference value of the explosion-proofness as to a resin container making up a gas detector.

Further, since the housing 10 or parts thereof can be integrally molded, the number of parts making up the gas detector can be reduced, so that a portable gas detector having excellent explosion-proofness can be provided at low cost.

Still further, the case body 10A and battery case 10B surrounding the space, in which the power source part and signal processing circuit are arranged, are formed by the specific static charge-controlling resin material, whereby the gas detector can be fabricated as one having an explosion-proof structure still higher in reliability.

Furthermore, since the gas detector is so constructed that power of 4.5 V is supplied from the 3 AA-sized (ANSI standard) dry cells 74 or the chargeable battery pack 90, comparatively great power as a portable gas detector is ensured, so that a contact combustion type gas sensor element can be used as at least one of the plurality of the gas sensors, whereby the degree of freedom of selection of detectable gas components becomes high, and high convenience for use can be achieved.

Although the preferred embodiments of the present invention have been described above, the present invention is not limited to the embodiments described above, and various changes and modifications may be added thereto.

For example, it is only necessary to form the functional part region in the foreside half portion within the housing of the gas detector and the battery part region in the rear half portion, and other members can be freely arranged. Dry cells used as a power source are not limited to the AA-sized (ANSI standard) dry cells.

The gas detector may be used by holding it with a hand, or by being fitted directly to a person's body or to a person's wear using a proper fitting member. As examples of the fitting member, may be mentioned a clip and a pin. The fitting member may be formed integrally with the housing according to the form thereof. The fitting member may be formed in an easily exchangeable shape.

The filter units for removal of interfering gases may be classified by coloring according to the functions thereof, i.e., the kinds of interfering gas components that can be removed, whereby proper filter units for removal of interfering gases corresponding to the gas sensors can be surely installed, and so gas detection can be conducted with high reliability.

The gas detector may also be so constructed that a communication terminal for reading out concentration data of gases detected by the gas detector is provided. In, for example, FIGS. 3 and 6, an aperture plate for infrared communication is indicated by reference numeral 19. According to such construction, the concentration date of the gases can be read out while conducting, for example, a charging operation of the gas detector.

The present invention will hereinafter be described specifically by the following examples and comparative examples. However, the present invention is not limited to these examples. Incidentally, all designations of "part" or "parts" and "%" as will be used in the following examples mean part or parts by weight and % by weight unless expressly noted.

<Preparation of Specimen>

Sample pellets were molded by an injection molding machine having clamping force of 80 tons to prepare a specimen. The molding was conducted under conditions of a cylinder temperature of 200 to 270° C. and a mold temperature of 30 to 60° C.

<Measurement of Physical Properties>

After the specimen was aged under an environment of room temperature (23±2° C.) and a relative humidity of 50%, it was subjected to measurement as to the following physical properties.

(1) Flexural Strength (Flexural Modulus of Elasticity):

The flexural modulus of elasticity was determined in accordance with ASTM D 760. The unit in the following Table is [MPa].

(2) Izod Impact Strength:

The Izod impact strength was determined in accordance with ASTM D 256 using a notched specimen having a thickness of ¼ in. The unit in the following Table is [J/m].

(3) Surface Resistivity:

The surface resistivity was measured in accordance with ASTM D 257 using the injection-molded specimen having a width of 6 cm, a length of 6 cm and a thickness of 0.3 cm by means of "Hiresta" manufactured by Mitsubishi Chemical Corporation.

(4) Insulation Resistance:

The insulation resistance was measured in accordance with the insulation resistance performance (Type Testing Guide of Explosion-Proof Construction Electromechanical Equipment; 1.2.2 Item: Technological Standard) of plastic parts required of the technological standard of explosion-proof electrical apparatus in Ministry of Health and Welfare. The measurement was conducted by using a specimen having a width of 60 mm and a length of 150 mm under conditions of a measuring temperature of 23° C., a measuring relative humidity of 50RH % and applied voltage of DC 500 V.

(5) Comparative Tracking Index:

The comparative tracking index was determined in accordance with Measurement of PTI Value of IEC 60112. The determination was conducted by using a specimen having a width of 30 mm, a length of 30 mm and a thickness of 3.2 mm under conditions of a measuring temperature of 21° C. and a measuring relative humidity of 45RH %.

(6) Moldability and Surface Smoothness:

Sample pellets were molded at a cylinder temperature of 200 to 270° C. and a mold temperature of 30 to 60° C. by means of an injection molding machine having clamping force of 220 tons using a 11-gate mold having a width of 13 cm, a length of 32 cm and a thickness of 0.5 cm to produce a molded product. The state of the molded product was observed to evaluate it in accordance with the following standard.

[Moldability]

The moldability (synthetic judgment by flowability, releasability, short shot, sprue breaking and the like) of a sample resin material was evaluated in accordance with the following standard:
 [A]: Very good;
 [B]: Moldable;
 [C]: Moldable, but a molding operation cannot be stably conducted;
 [D]: Immoldable.

[Appearance (Surface Smoothness) of Molded Product]

The synthetic judgment of a sample molded product by smoothness, uneven luster, weld mark, flash mark, fuzz and the like was evaluated visually in accordance with the following standard:
 [A]: Very good;
 [B]: Usable;
 [C]: Usable in a general-purpose part, but unsuitable for a precision part;
 [D]: Unusable.

Materials used in the examples are as follows:

<Thermoplastic Resin>

Thermoplastic Resin for Component (A):
 (A-1): ABS resin ("Techno ABS330", trade name; product of Techno Polymer Co., Ltd.).

Thermoplastic Resin for Component (B):
 (B-1): Polycarbonate resin ("Iupilon S-2000", trade name).

(B-2): Polystyrene resin ("GPPSG8259", trade name; product of A & M Styrene Co., Ltd.).

Mixed Resin of Components (A) and (B):
 (A+B): ABS/PC composite resin ("EXCELLOY CK10", trade name; product of Techno Polymer Co., Ltd.; ABS/PC alloy grade, ABS/PC=2/1, particle diameter of each component: 500 nm to 100 µm (as a result of measurement from a microphotograph of a molded product obtained by molding the resin at a temperature of 220° C.)).

Thermoplastic Resin for Component (C):
 (C-1): Poly(ether ester amide) ("Pelestat NC6321", trade name; product of Sanyo Chemical Industries, Ltd.; Tg: −45° C. to −55° C.).

<Metal Salt>

Component (D):
 (D-1): Bis(trifluoromethanesulfonyl)imidolithium [$(CF_3SO_2)_2$Nli].

<Other Components>
 Organic compound: Bis[2-(2-butoxyethoxy)ethyl] adipate.
 Inorganic filler: Talc ("Talc TT", trade name; product of Takehara Kagaku K.K.; average particle diameter: 7 µm).

EXAMPLE 1

Eighty-five parts by weight of (A+B), 15 parts by weight of (C-1), 0.2 parts by weight of (D-1) and 0.8 parts by weight of bis[2-(2-butoxyethoxy)ethyl] adipate were preliminarily dry-blended by a tumbling mixer, and the resultant dry blend was melted and kneaded at a melting temperature of 220 to 270° C. by a co-direction twin-screw extruder having a barrel diameter of 47 mm. A string-like molten resin mixture extruded from a die was cooled in a water tank and chopped by a cutter to prepare pellets of a static charge-controlling resin composition. The result is shown in Table 1.

EXAMPLE 2

Sixty-five parts by weight of (A+B), 35 parts by weight of (C-1), 0.7 parts by weight of (D-1), 3.8 parts by weight of bis[2-(2-butoxyethoxy)ethyl] adipate and 15 parts by weight of talc were preliminarily dry-blended by a tumbling mixer, and the resultant dry blend was melted and kneaded at a melting temperature of 220 to 270° C. by a co-direction twin-screw extruder having a barrel diameter of 47 mm. A string-like molten resin mixture extruded from a die was cooled in a water tank and chopped by a cutter to prepare pellets of a static charge-controlling resin composition. The result is shown in Table 1.

EXAMPLE 3

After 40 parts by weight of (A-1) and 40 parts by weight of (B-1) were melted and kneaded at a melting temperature of 240 to 270° C. by a co-direction twin-screw extruder having a barrel diameter of 47 mm to prepare pellets, 20 parts by weight of (C-1), 0.2 parts by weight of (D-1) and 0.8 parts by weight of bis[2-(2-butoxyethoxy)ethyl] adipate were preliminarily dry-blended with the above-prepared pellets by a tumbling mixer, and the resultant dry blend was melted and kneaded at a melting temperature of 220 to 270° C. by a co-direction twin-screw extruder having a barrel diameter of 47 mm. A string-like molten resin mixture extruded from a die was cooled in a water tank and chopped by a cutter to prepare pellets of a static charge-controlling resin composition. The result is shown in Table 1.

EXAMPLE 4

Twenty-eight parts by weight of (A-1), 65 parts by weight of (B-2), 7 parts by weight of (C-1), 0.2 parts by weight of (D-1) and 0.8 parts by weight of bis[2-(2-butoxyethoxy)ethyl] adipate were preliminarily dry-blended by a tumbling mixer, and the resultant dry blend was melted and kneaded at a melting temperature of 240 to 270° C. by a co-direction twin-screw extruder having a barrel diameter of 47 mm. A string-like molten resin mixture extruded from a die was cooled in a water tank and chopped by a cutter to prepare pellets of a static charge-controlling resin composition. The result is shown in Table 1.

COMPARATIVE EXAMPLE 1

Example where No Component (B) was Blended

Eighty-five parts by weight of (A-1), 15 parts by weight of (C-1), 0.2 parts by weight of (D-1) and 0.8 parts by weight of bis[2-(2-butoxyethoxy)ethyl] adipate were preliminarily dry-blended by a tumbling mixer, and the resultant dry blend was melted and kneaded at a melting temperature of 240 to 270° C. by a co-direction twin-screw extruder having a barrel diameter of 47 mm. A string-like molten resin mixture extruded from a die was cooled in a water tank and chopped by a cutter to prepare pellets of a static charge-controlling resin composition. The result is shown in Table 1.

COMPARATIVE EXAMPLE 2

Example where No Component (A) was Blended

Ninety-three parts by weight of (B-1), 7 parts by weight of (C-1), 0.2 parts by weight of (D-1) and 0.8 parts by weight of bis[2-(2-butoxyethoxy)ethyl] adipate were preliminarily dry-blended by a tumbling mixer, and the resultant dry blend was melted and kneaded at a melting temperature of 240 to 270° C. by a co-direction twin-screw extruder having a barrel diameter of 47 mm. A string-like molten resin mixture extruded from a die was cooled in a water tank and chopped by a cutter to prepare pellets of a static charge-controlling resin composition. The result is shown in Table 1.

As apparent from the results described above, it was confirmed that the static charge-controlling resin compositions according to Examples 1 to 4 fundamentally have excellent mechanical properties (flexural modulus of elasticity and flexural strength) and moreover have excellent moldability and surface smoothness and besides excellent static charge-controlling ability. The resin compositions are thereby extremely useful as materials forming a housing of a portable gas detector or component parts thereof.

On the other hand, it was confirmed that the static charge-controlling resin compositions according to Comparative Examples 1 and 2 have excellent mechanical properties (flexural modulus of elasticity and flexural strength) and moreover have excellent moldability and surface smoothness, but do not sufficiently develop the static charge-controlling ability satisfying the standard as to the explosion-proofness related to portable gas detectors because their insulation resistance values are as extremely great as at least 1 GΩ.

What is claimed is:

1. An explosion-proof portable gas detector comprising: a gas sensor, a signal processing circuit for processing output signals from the gas sensor, a display mechanism for displaying the result of gas detection by the gas sensor and a power source part for driving the signal processing circuit and display mechanism, arranged within a housing in the form of a slim and flat box holdable by grasping with a hand,
   wherein the whole or a part of the housing is formed of a static charge-controlling resin material having an insulating resistance value of at most 1 GΩ and a comparative tracking index of at least 90 V.

2. The explosion-proof portable gas detector according to claim 1, wherein the static charge-controlling resin material contains a mixed resin component composed of a combination of a component (A) composed of a thermoplastic resin, a component (B) composed of a thermoplastic resin incompatible with the component (A) at a molecular level and a component (C) composed of a thermoplastic resin other than the thermoplastic resin of components (A) and (B), which has a polar group, and a component CD) composed of a metal salt formed by a cation derived from an alkali metal or alkaline earth metal and an anion capable of ionically dissociating, and
   wherein a proportion of the component (C) is 45 down to 2 % by weight based on the mixed resin component,

|  | Component | Material | Example 1 | Example 2 | Example 3 | Example 4 | Comparative example 1 | Comparative example 2 |
|---|---|---|---|---|---|---|---|---|
| Blending prescription (parts by weight) | (A) + (B) | Excelloy CK10 | 85 | 65 | | | | |
| | (A-1) | Techno ABS330 | | | 40 | 28 | 85 | |
| | (B-1) | Iupilon S-2000 | | | 40 | | | |
| | (B-2) | PS | | | | 65 | | 93 |
| | (C-1) | PEEA(Pelestat NC6321) | 15 | 35 | 20 | 7 | 15 | 7 |
| | (D-1) | $(CF_3SO_2)_2NLi$ | 0.2 | 0.7 | 0.2 | 0.2 | 0.2 | 0.2 |
| | Other | Bis[2-(2butoxyethoxy)ethyl]adipate | 0.8 | 3.8 | 0.8 | 0.8 | 0.8 | 0.8 |
| | Other | Talc TT | | | 15 | | | |
| | | Flexural strength [MPa] | 1,700 | 1,000 | 1,600 | 1,900 | 1,800 | 2,400 |
| | | Izod impact strength [J/m] | 600 | 250 | 400 | 80 | 80 | 15 |
| | | Surface resistivity [Ω/sq.] | $5 \times 10^9$ | $1 \times 10^8$ | $2 \times 10^9$ | $1 \times 10^{10}$ | $9 \times 10^9$ | $6 \times 10^1$ |
| | | Insulation resistance [GΩ] | 0.4 | 0.01 | 0.1 | 1 | at least 1 | at least 1 |
| | | Comparative tracking index [V] | 600 | at least 100 | 600 | at least 100 | 600 | at least 100 |
| | | Moldability | A | A | A | A | A | A |
| | | Surface smoothness | A | A | A | A | A | A | and a proportion of the component (D) per 100 parts by weight of the mixed resin component is 0.01 to 5 parts by weight.

3. The explosion-proof portable gas detector according to claim 2, wherein the static charge-controlling resin is such that the resin components of both component (A) and component (B) are in a state dispersed in a structural unit diameter ranging from 50 nm to 500 μm when the thermoplastic resin making up the component (A) and the thermoplastic resin making up the component (B) are melted and kneaded at a temperature higher than the melting temperatures of the respective components.

4. The explosion-proof portable gas detector according to claim 1 or 2, wherein the housing is formed of a molded product of the static charge-controlling resin material.

5. The explosion-proof portable gas detector according to claim 3, wherein the housing is formed of a molded product of the static charge-controlling resin material.

6. The explosion-proof portable gas detector according to claim 1 or 2, wherein a gas suction pump to feed a gas to be detected from the outside to the gas sensors by suction is provided within the housing.

7. The explosion-proof portable gas detector according to claim 3, wherein a gas suction pump to feed a gas to be detected from the outside to the gas sensors by suction is provided within the housing.

8. The explosion-proof portable gas detector according to claim 5, wherein a gas suction pump to feed a gas to be detected from the outside to the gas sensors by suction is provided within the housing.

9. The explosion-proof portable gas detector according to claim 1 or 2, wherein a plurality of gas sensors, at least one of which is composed of a contact combustion type gas sensor element, are provided, and power of 4.5 V is supplied from the power source part.

10. The explosion-proof portable gas detector according to claim 3, wherein a plurality of gas sensors including at least a gas sensor composed of a contact combustion type gas sensor element are provided, and power of 4.5 V is supplied from the power source part.

11. The explosion-proof portable gas detector according to claim 5, wherein a plurality of gas sensors including at least one gas sensor composed of a contact combustion type gas sensor element are provided, and power of 4.5 V is supplied from the power source part.

12. The explosion-proof portable gas detector according to claim 8, wherein a plurality of gas sensors including at least a gas sensor composed of a contact combustion type gas sensor element are provided, and power of 4.5 V is supplied from the power source part.

13. The explosion-proof portable gas detector according to claim 1 or 2, wherein a foreside half portion in the interior of the housing is provided as a functional part region, in which functional members related to a gas detecting operation are arranged, and a rear half portion in the interior of the housing is provided as a battery part region, in which a power source for driving the functional members is arranged, and wherein a battery chamber is formed in the battery part region so as to be opened to the back surface of the housing, and either one of three rod-like dry cells or a rechargeable battery pack formed by holding three rechargeable batteries having the same external shape as the dry cell by a holding frame member in a state arranged in parallel is installed in the battery chamber exchangeably with the other.

14. The explosion-proof portable gas detector according to claim 3, wherein a foreside half portion in the interior of the housing is provided as a functional part region, in which functional members related to a gas detecting operation are arranged, and a rear half portion in the interior of the housing is provided as a battery part region, in which a power source for driving the functional members is arranged, and wherein a battery chamber is formed in the battery part region so as to be opened to the back surface of the housing, and either one of three rod-like dry cells or a rechargeable battery pack formed by holding three rechargeable batteries having the same external shape as the dry cell by a holding frame member in a state arranged in parallel is installed in the battery chamber exchangeably with the other.

15. The explosion-proof portable gas detector according to claim 5, wherein a foreside half portion in the interior of the housing is provided as a functional part region, in which functional members related to a gas detecting operation are arranged, and a rear half portion in the interior of the housing is provided as a battery part region, in which a power source for driving the functional members is arranged, and wherein a battery chamber is formed in the battery part region so as to be opened to the back surface of the housing, and either one of three rod-like dry cells or a rechargeable battery pack formed by holding three rechargeable batteries having the same external shape as the dry cell by a holding frame member in a state arranged in parallel is installed in the battery chamber exchangeably with the other.

16. The explosion-proof portable gas detector according to claim 8, wherein a foreside half portion in the interior of the housing is provided as a functional part region, in which functional members related to a gas detecting operation are arranged, and a rear half portion in the interior of the housing is provided as a battery part region, in which a power source for driving the functional members is arranged, and wherein a battery chamber is formed in the battery part region so as to be opened to the back surface of the housing, and either one of three rod-like dry cells or a rechargeable battery pack formed by holding three rechargeable batteries having the same external shape as the dry cell by a holding frame member in a state arranged in parallel is installed in the battery chamber exchangeably with the other.

17. The explosion-proof portable gas detector according to claim 12, wherein a foreside half portion in the interior of the housing is provided as a functional part region, in which functional members related to a gas detecting operation are arranged, and a rear half portion in the interior of the housing is provided as a battery part region, in which a power source for driving the functional members is arranged, and wherein a battery chamber is formed in the battery part region so as to be opened to the back surface of the housing, and either one of three rod-like dry cells or a rechargeable battery pack formed by holding three rechargeable batteries having the same external shape as the dry cell by a holding frame member in a state arranged in parallel is installed in the battery chamber exchangeably with the other.

18. The explosion-proof portable gas detector according to claim 17, wherein terminals for charging for the recharge able battery pack are provided on the housing in a state exposed to the external surface thereof.

19. The explosion-proof portable gas detector according to claim 18, wherein the rechargeable battery pack is such that a positive terminal is formed at one end thereof, and a negative terminal is formed at the other end, and the detector has a function of judging which of the dry cells or the rechargeable battery pack is installed in a battery chamber by detecting the number of terminals that electrical connection has been achieved.

* * * * *